(12) United States Patent
Cane'

(10) Patent No.: US 8,172,814 B2
(45) Date of Patent: May 8, 2012

(54) SYRINGE PLUNGER AND SYRINGE INCORPORATING THE PLUNGER

(75) Inventor: Mario Cane', Collegno (IT)

(73) Assignee: Cane' S.p.A., Rivoli (IT)

( * ) Notice: Subject to any disclaimer, the term of this patent is extended or adjusted under 35 U.S.C. 154(b) by 222 days.

(21) Appl. No.: 12/514,543

(22) PCT Filed: Nov. 14, 2007

(86) PCT No.: PCT/IB2007/054627
§ 371 (c)(1),
(2), (4) Date: May 12, 2009

(87) PCT Pub. No.: WO2008/059448
PCT Pub. Date: May 22, 2008

(65) Prior Publication Data
US 2010/0057014 A1     Mar. 4, 2010

(30) Foreign Application Priority Data

Nov. 16, 2006  (IT) .............................. TO2006A0816

(51) Int. Cl.
*A61M 5/315* (2006.01)
(52) U.S. Cl. ....................................... 604/228
(58) Field of Classification Search .............. 604/187, 604/218, 228
See application file for complete search history.

(56) References Cited

U.S. PATENT DOCUMENTS

| | | | | |
|---|---|---|---|---|
| 4,677,980 A * | 7/1987 | Reilly et al. | ................ | 600/432 |
| 4,911,695 A * | 3/1990 | Lindner | ................ | 604/228 |
| 4,931,043 A * | 6/1990 | Ray et al. | ................ | 604/228 |
| 4,973,308 A * | 11/1990 | Borras et al. | ................ | 604/110 |
| 4,973,309 A * | 11/1990 | Sultan | ................ | 604/110 |
| 5,084,017 A * | 1/1992 | Maffetone | ................ | 604/110 |
| 5,085,639 A * | 2/1992 | Ryan | ................ | 604/110 |
| 5,094,148 A * | 3/1992 | Haber et al. | ................ | 92/29 |
| 5,181,912 A * | 1/1993 | Hammett | ................ | 604/110 |
| 5,352,200 A | 10/1994 | Hammett et al. | | |
| 5,413,563 A * | 5/1995 | Basile et al. | ................ | 604/218 |
| 5,423,757 A * | 6/1995 | Olovson et al. | ................ | 604/110 |
| 5,593,386 A * | 1/1997 | Helldin | ................ | 604/110 |
| 5,624,408 A * | 4/1997 | Helldin | ................ | 604/224 |
| 5,688,252 A * | 11/1997 | Matsuda et al. | ................ | 604/218 |
| 5,947,929 A * | 9/1999 | Trull | ................ | 604/152 |
| 5,947,935 A * | 9/1999 | Rhinehart et al. | ................ | 604/218 |
| 6,017,330 A * | 1/2000 | Hitchins et al. | ................ | 604/218 |
| 6,120,479 A * | 9/2000 | Campbell et al. | ................ | 604/110 |
| 6,447,487 B1 * | 9/2002 | Cane' | ................ | 604/181 |

(Continued)

FOREIGN PATENT DOCUMENTS

EP          0 925 798 A2      6/1999

(Continued)

*Primary Examiner* — Jackie Ho
*Assistant Examiner* — William Carpenter
(74) *Attorney, Agent, or Firm* — Sughrue Mion, PLLC

(57) ABSTRACT

A plunger (13) for a syringe (11), comprising a cylindrical hollow body having a closed base and an opening located at the opposite base of said hollow body, wherein a seat accessible through said opening is provided to receive the head of a rod or a pusher (15), said seat being equipped with engagement means for retaining said head inside the seat at the end of an axial translational or an axial translational and rotary coupling movement. The application further concerns the rod intended to be associated with said plunger and a syringe or a phial using the plunger.

7 Claims, 7 Drawing Sheets

U.S. PATENT DOCUMENTS

| | | | |
|---|---|---|---|
| 6,663,593 B2 * | 12/2003 | Ito | 604/110 |
| 6,676,642 B2 * | 1/2004 | Beebe | 604/228 |
| 6,764,466 B1 * | 7/2004 | Staats et al. | 604/154 |
| 6,773,416 B1 * | 8/2004 | Hsu | 604/110 |
| 7,033,338 B2 * | 4/2006 | Vilks et al. | 604/228 |
| 7,798,377 B2 * | 9/2010 | Imhof et al. | 222/386 |
| 7,798,993 B2 * | 9/2010 | Lim et al. | 604/110 |
| 8,038,656 B2 * | 10/2011 | Lloyd et al. | 604/228 |
| 2004/0225263 A1 * | 11/2004 | Chen | 604/228 |
| 2005/0113754 A1 | 5/2005 | Cowan | |

FOREIGN PATENT DOCUMENTS

| | | |
|---|---|---|
| EP | 1 078 643 A1 | 2/2001 |
| WO | 2006/087762 A1 | 8/2006 |

* cited by examiner

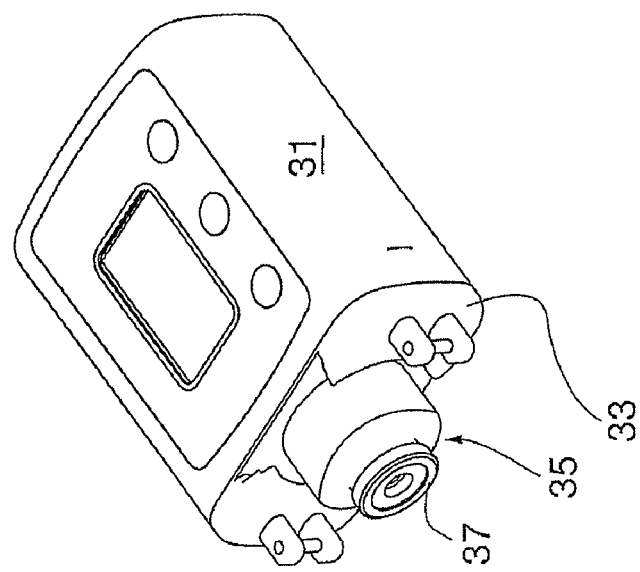
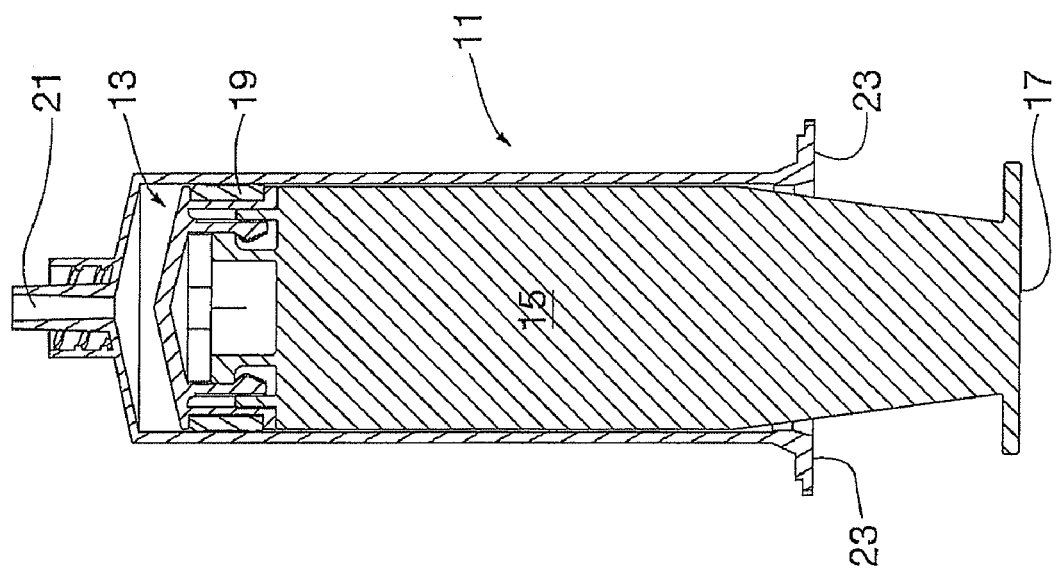

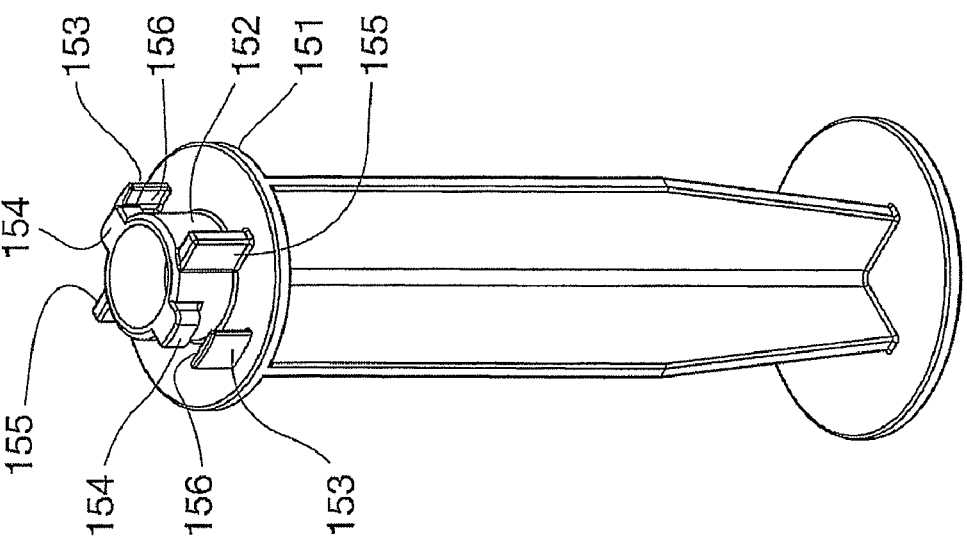
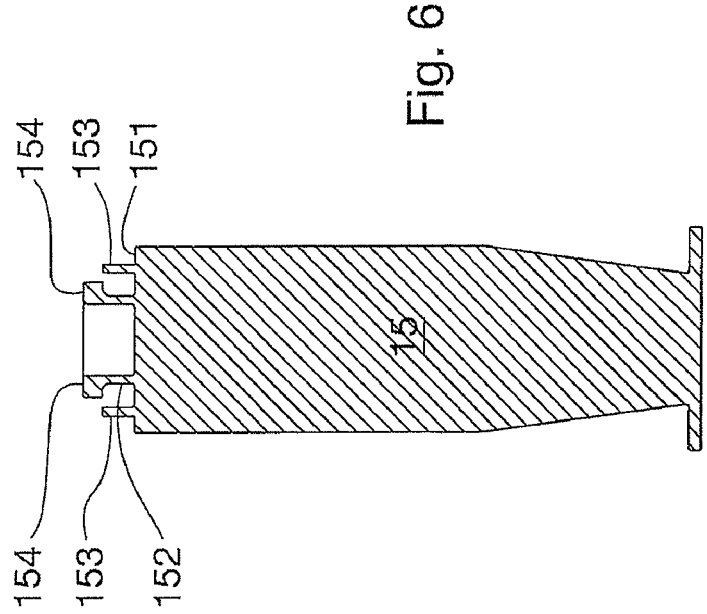
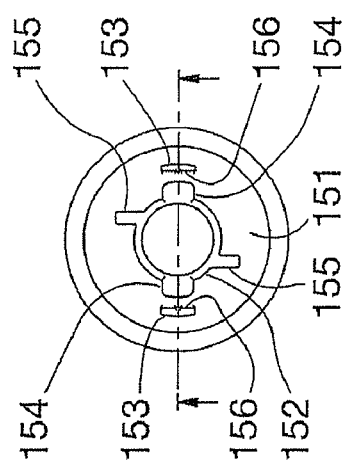

SYRINGE PLUNGER AND SYRINGE INCORPORATING THE PLUNGER

The present invention relates to a syringe plunger and to a syringe incorporating such plunger.

More precisely, the invention relates to a plunger for a syringe or a small bottle (phial), e.g. a syringe for drug injection, and more particularly for a syringe actuated by an infusion pump, e.g. a drug infusion pump.

It is known that syringes in general, and in particular syringes for drug infusion, which generally are of disposable type, comprise a hollow cylindrical body (barrel) within which a plunger slides, which can be made of elastomeric material or of plastics and is equipped with a corresponding gasket of elastomeric material.

It is also known that the plunger is axially slidable within the syringe barrel in a first direction in order to draw liquid through a first opening provided at one end of the syringe barrel, and in a second direction to inject, through the same opening, the liquid previously drawn.

Generally, sliding of the plunger within the syringe barrel is manually obtained by acting on a rod connected with the plunger and projecting from the syringe barrel through a second opening, provided at the opposite end of the syringe barrel with respect to the first opening.

In other cases, sliding of the plunger is obtained by means of an electro-mechanical device that, in case of drug infusion, is called "infusion pump".

A drug infusion pump is an electro-mechanical device comprising an electric motor and corresponding mechanical members organised so as to cause axial extension of a pusher, which pushes the syringe plunger and causes the drug contained in the syringe to be gradually delivered therefrom.

The state of the art in the field of drug infusion pumps provides a wide range of devices, for application both to patients confined to bed and to patients who can freely walk and perform a substantially normal physical activity.

An example of portable pump is disclosed in EP 1078643 in the name of the Applicant.

In syringes intended for use with certain kinds of drug infusion pumps, the rod making the plunger slide must be separable from the plunger. Indeed, once the syringe has been filled with the drug by acting on the rod and the plunger associated therewith, the rod must be removed in order to enable coupling the syringe with the pump and to cause the pump pusher, when extending during pump operation, to make the syringe plunger slide, thereby causing drug delivery.

In order to avoid dangerous risks of free drug flow, i.e. a flow that is determined by the pressure fall between the level at which the pump is located and the patient instead of being determined by the slow and regular push by the pump pusher, the syringe plunger must be coupled with the pusher head in sufficiently stable manner.

One of the problems encountered when using syringes in drug infusion pumps is thus making the coupling between the pusher head and the syringe plunger sufficiently stable and safe.

EP 1078643 in the name of the Applicant discloses a solution to the above problem, according to which the head of the pump pusher has a knurled outer surface improving the engagement with the elastomeric material of the plunger.

Such a solution is satisfactory for plungers made of rubber, but it could not be employed with favourable results in syringes equipped with plungers made of plastics.

Use of plastics has several advantages in pharmaceutical field, since plastics is more inert to drugs and biological liquids and reduces the problems resulting from rubber deformation.

Natural rubber or butyl rubber actually has some drawbacks, since it contains chemical components, introduced during working and during curing process, which tend to exude to the surface of the plunger during the contact with the liquid contained in the syringe.

Such exudates present at the surface of the plunger are harmful and particularly undesirable when the syringe is used for drug injection or when a biological liquid, such as blood, is withdrawn from a patient. The problem is further aggravated in cases of phials prefilled with drug and undergoing a long-term storage before use, since the amount of exudates will be unavoidably greater.

Syringes having a plunger made of plastics and equipped with an elastomeric seal are at present in use especially, but not only, in medical field: indeed, plastics alone would not be able to ensure, in some applications, a sufficient seal against the syringe barrel.

An example of syringe having a plunger made of plastics is disclosed in document EP 0925798.

According to the teaching of that document, the syringe plunger can be coupled with its rod through a rotary movement, thanks to a threaded joint.

The threaded coupling however is not suitable for an easy association of the syringe plunger to the pusher of a drug infusion pump, since the operation, which generally is carried out by the patient, who often is aged and/or in poor health conditions, should take place when the syringe is full of drug and would entail rotation of the syringe or the pump.

The present invention aims therefore at solving the problem of making the coupling between the head of the pusher of a pump and the plunger of a syringe easy and stable.

This object of the invention is achieved by means of the plunger as claimed in the appended claims.

Advantageously, thanks to the provision of engagement means inside a seat formed within the plunger and accessible from the outside, the pusher of a drug infusion pump can be coupled with the plunger through a simple axial translational movement bringing the two parts closer together.

Similarly, according to the invention, still thanks to the provision of engagement means inside a seat formed within the plunger and accessible from the outside, a syringe rod can be coupled with the plunger by combining a simple axial translational movement bringing the two parts closer together with a subsequent rotary movement by few degrees, typically less than 90°.

Advantageously moreover, according to the invention, the plunger and the pusher or the plunger and the rod can be easily disconnected by performing the above operations in the reverse direction.

A further advantage of the invention results from the simple construction of the engagement means provided inside the seat in the plunger, since the same means enable retaining both the pusher of an infusion pump and the syringe rod.

The above objects will become more apparent from the description of a preferred embodiment of the invention, given by way of non limiting example with reference to the accompanying drawings, in which:

FIG. 1 is a longitudinal sectional view of the syringe according to the invention;

FIG. 2 is a perspective view of an infusion pump;

FIG. 6 is a longitudinal sectional view of the rod of the syringe shown in FIG. 1;

FIG. 7 is a top view of the rod shown in FIG. 6;

FIG. 8 is a perspective view of the rod shown in FIG. 6.

Figure 4B:
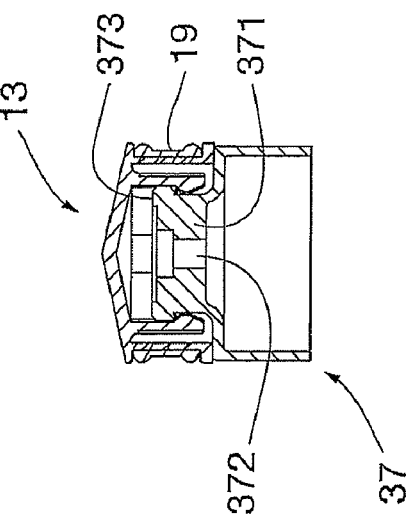
FIG. 4b is a sectional view of the plunger and the pusher shown in FIG. 4a, taken along line 4b-4b.
Figure 4A:
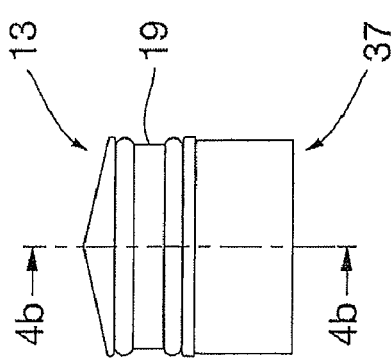
FIG. 4a is a side view of the plunger of the syringe shown in FIG. 1, associated with the pusher.

Referring to FIG. 1, there is shown a sectional view of a syringe 1, of the kind used for instance for drug infusion, comprising a plunger 13 associated with a rod 15 that can be used to make plunger 13 slide by manually acting on rod end 17.

Plunger 13 is preferably of the kind made of thermoplastic material, equipped with a ring-shaped sealing gasket 19, for instance made of elastomeric material, arranged between the body of plunger 13 and the inner wall of the cylindrical barrel of syringe 11.

Plunger 13 is slidable within the barrel of syringe 11 in a first direction in order to draw liquid through a first opening 21 provided at one end of the barrel of syringe 11, and in a second direction, opposite to the first one, to inject, through the same opening 21, the liquid previously drawn.

Referring to FIG. 2, there is shown a generic portable pump 31 for drug infusion, equipped with a nut 33 for receiving rear wings 23 of a syringe 11 and consequently enabling the syringe to be associated with the pump, and with a pusher 35 having a head 37 shaped so as to be able to engage the plunger of a syringe associated with the pump.

Figure 3B:
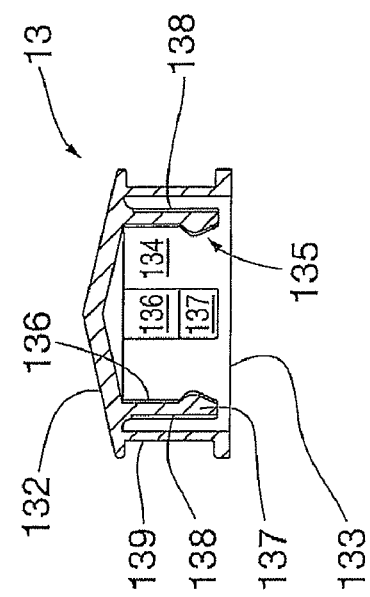
FIG. 3b is a sectional view of the plunger shown in FIG. 3a, taken along line 3b-3b.
Figure 3A:
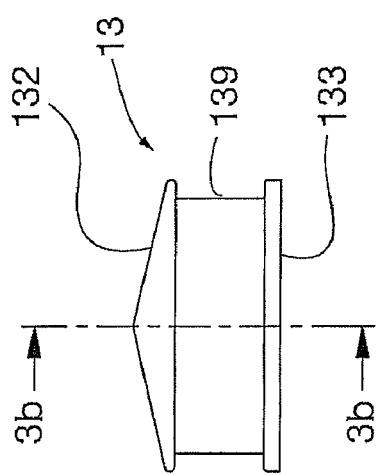
FIG. 3a is a side view of the plunger of the syringe shown in FIG. 1, without the gasket.
Figure 5:
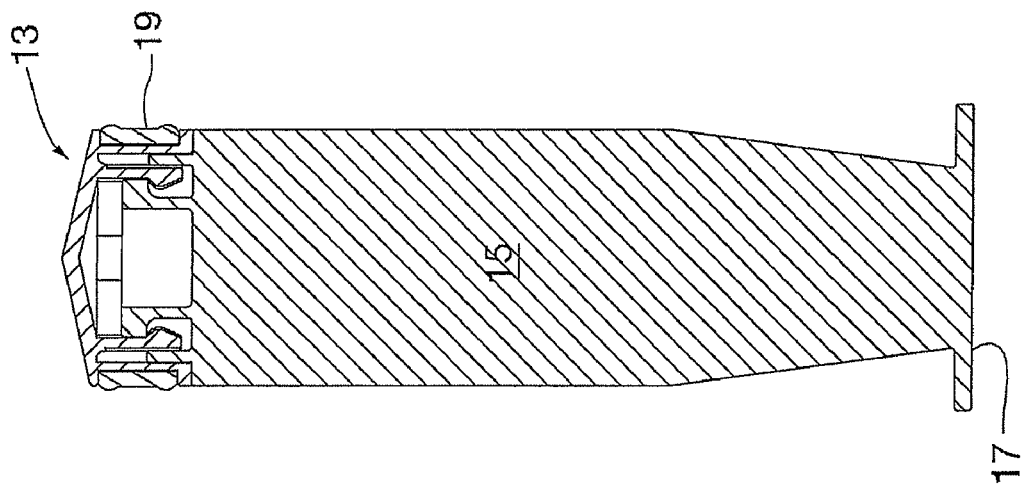
FIG. 5 is a longitudinal sectional view of the plunger and the rod of the syringe shown in FIG. 1.

Turning now to FIGS. 3a and 3b, plunger 13 comprises a corresponding hollow cylindrical body in which a dome 132 closing one the cylinder bases and an opening 133 formed in the opposite base are defined. A circumferential groove 139 is provided around the cylindrical body of plunger 13 to accommodate ring-shaped gasket 19.

A seat 134 is provided inside plunger 13 and has defined therein the joint for the head of rod 15 and/or, as it will disclosed later on, for the head of the pusher of an infusion pump.

In the example illustrated, the joint defined inside seat 134 of plunger 13 is formed by four longitudinal extensions 135, arranged along a circumference and mutually spaced apart by 90°.

In the alternative, said joint could be formed externally of the body of plunger 13, in which case extensions 135 will be located externally of the body of plunger 13, which preferably will be closed at both ends.

For reasons that will be better understood later on, each extension 135 has a stem 136 secured to dome 132 internally of seat 134 and ending in a tooth 137 radially directed towards the centre of seat 134, and a longitudinal groove 138 formed on the face of stem 136 opposite to tooth 137.

Referring to FIGS. 4a to 4d, there is shown the situation of use of plunger 13 coupled with head 37 of pusher 35 of a drug infusion pump, such as pump 31 shown in FIG. 2.

Advantageously, thanks to the joint defined inside seat 134, plunger 13 can accommodate head 37 of the pusher of a drug infusion pump between longitudinal extensions 135.

Still referring to FIGS. 4a to 4d, head 37 of pusher 35 of a drug infusion pump generally comprises a cylindrical body 371, having an axial bore 372 enabling fastening head 37 to the rod (not shown) of the pusher of the pump, by means of a screw or other fastening means. The outer end of the cylindrical body of head 37 further has a widened edge 373 that, in case of plungers made of rubber, enables retaining the plunger against the pusher head thanks to the deformation of the material, in order to hinder phenomena of free flow.

Advantageously, according to the invention, the widened edge of head 37 is retained inside seat 134 of plunger 13 thanks to teeth 137 provided at the base of longitudinal extensions 135 that, in order to enable insertion of head 37, will preferably be resiliently flexible in radial direction towards the outside of seat 134.

Advantageously, teeth 137 prevent plunger 13 from being disconnected from head 37 of the pusher in axial direction, thereby avoiding the danger of free flow of the drug while the pump is being used in its normal operating conditions.

Application in axial direction of a force higher than the force that could determine free flow phenomena allows instead an easy separation of the plunger from the pump at the end of the delivery of the drug.

Figure 4D:
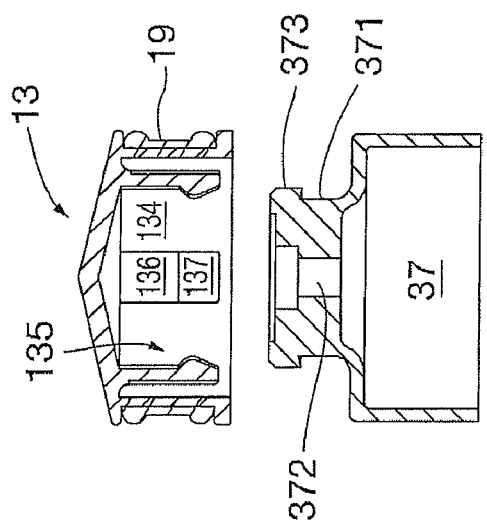
FIG. 4d is a sectional exploded view of the plunger and the pusher shown in FIG. 4c, taken along line 4d-4d.
Figure 4C:
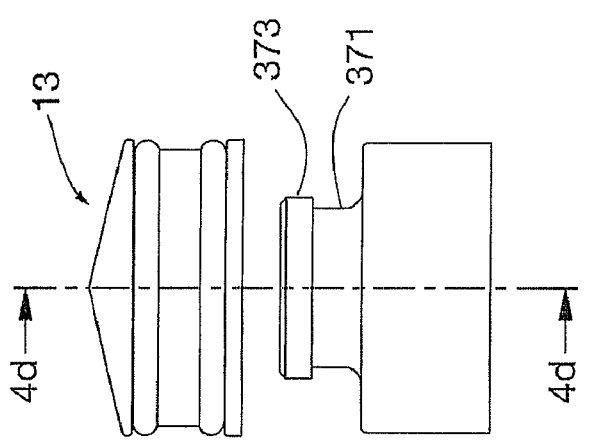
FIG. 4c is an exploded view of the plunger of the syringe shown in FIG. 1 and of the pusher.
Figure 4E:
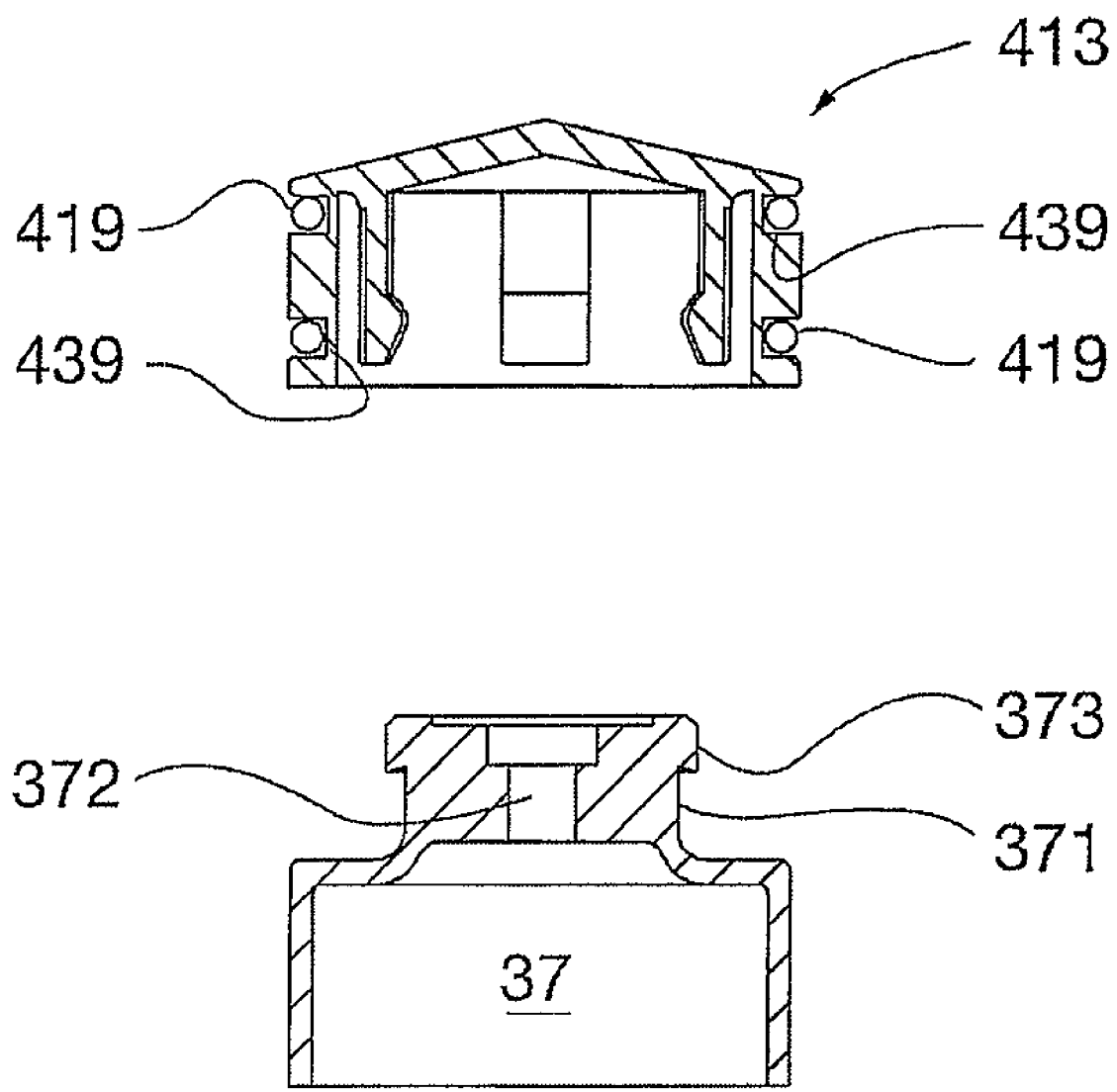
FIG. 4e is an exploded view similar to FIG. 4d and showing a first variant embodiment of the plunger.

Turning to FIG. 4e, there is shown a first variant embodiment of the plunger, here generally denoted 413.

According to that variant embodiment, plunger 413 has a pair of circumferential grooves 439 for receiving respective O-rings 419.

Also in that embodiment, plunger 413 can advantageously be made of thermoplastic material with gaskets 419 made of elastomeric material in order to ensure the necessary seal.

Turning now to FIGS. 5 to 8, rod 15 of the syringe according to the invention is shown in greater detail. The rod comprises, at its forward end intended to engage plunger 13, a disc-shaped base 151 from which a central cylindrical projection 152 and a pair of diametrically opposite arc-shaped projections 153, located externally of projection 152, extend axially upwards.

There is provided a first pair of radial stops 154, radially extending from the forward base of cylindrical projection 152, and a second pair of axial stops 155 extending from the side wall of projection 152, said axial stops being joined to the disc-shaped base. In the alternative, said axial stops can be joined only either to base 151 or to cylindrical projection 152.

For reasons that will be explained later on, arc-shaped projections 153 include a central longitudinal projection 156, radial stops 154 are arranged along a diameter passing through the central axis of cylindrical projection 152 and axial stops 155 are mutually offset, that is they are arranged along the direction of two respective chords of cylindrical projection 152.

Coupling of rod 15 with plunger 13 takes place through a first translational movement bringing the two parts closer together in axial direction, during which movement cylindrical projection 152, arc-shaped projections 153, radial stops 154 and axial stops 155 penetrate into seat 134, and through a second rotary movement, at the end of which radial stops 154 are located in correspondence of two respective longitudinal extensions 135 of plunger 13, axial stops 155 abut against the other two extensions and arc-shaped projections 153 are located in correspondence of the two first-mentioned longitudinal extensions 135, with their respective longitudinal extensions engaged within the corresponding grooves 138.

In such a configuration, teeth 137 of extensions 135 located in correspondence of radial stops 154 prevent the rod from disconnecting from the plunger while the drug is being drawn into the syringe. Rotation of the rod relative to the plunger at the end of the drawing of the drug and the subsequent separation are on the contrary simple operations that can be easily carried out even by aged patients.

Figure 4F:
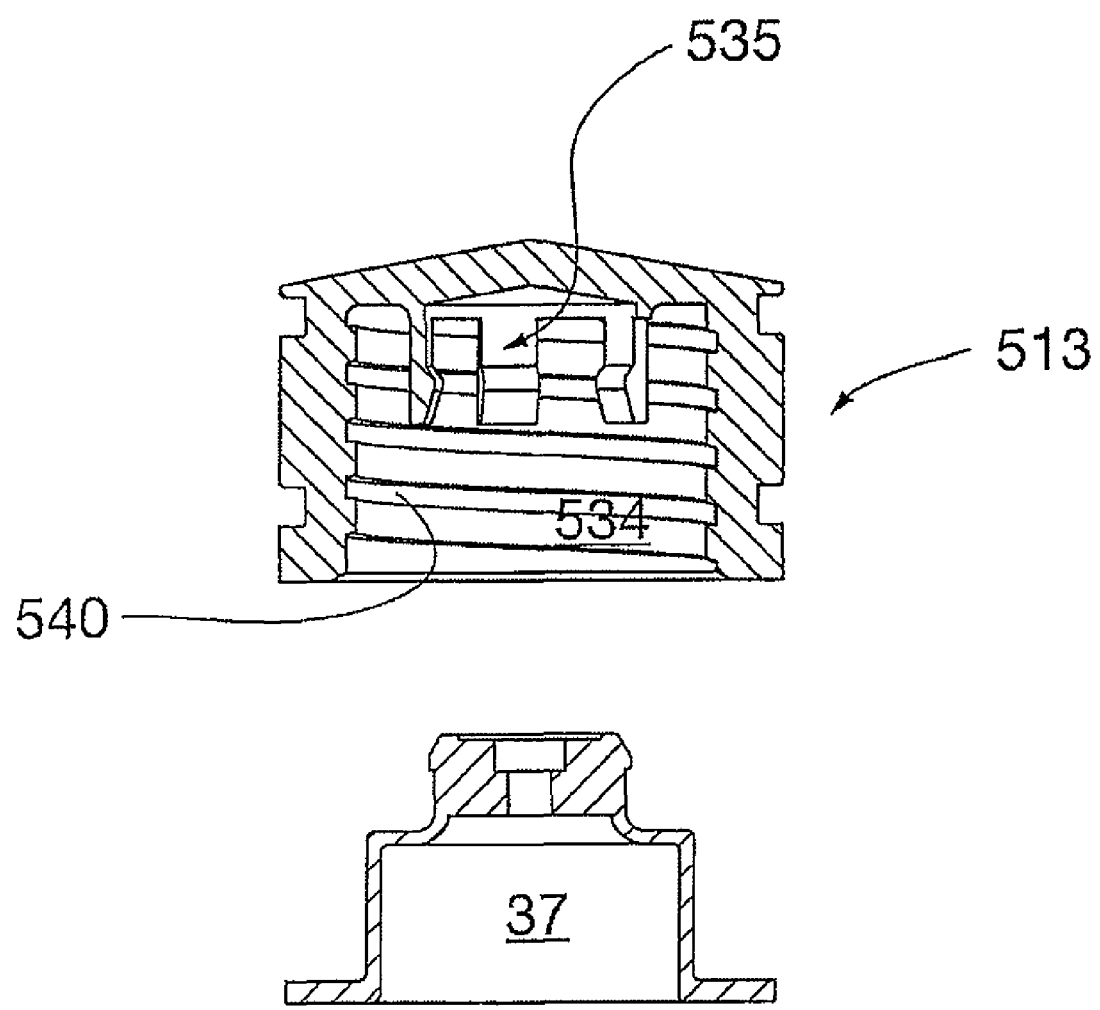
FIG. 4f is an exploded view similar to FIG. 4d and showing a second variant embodiment of the plunger.
Figure 4G:
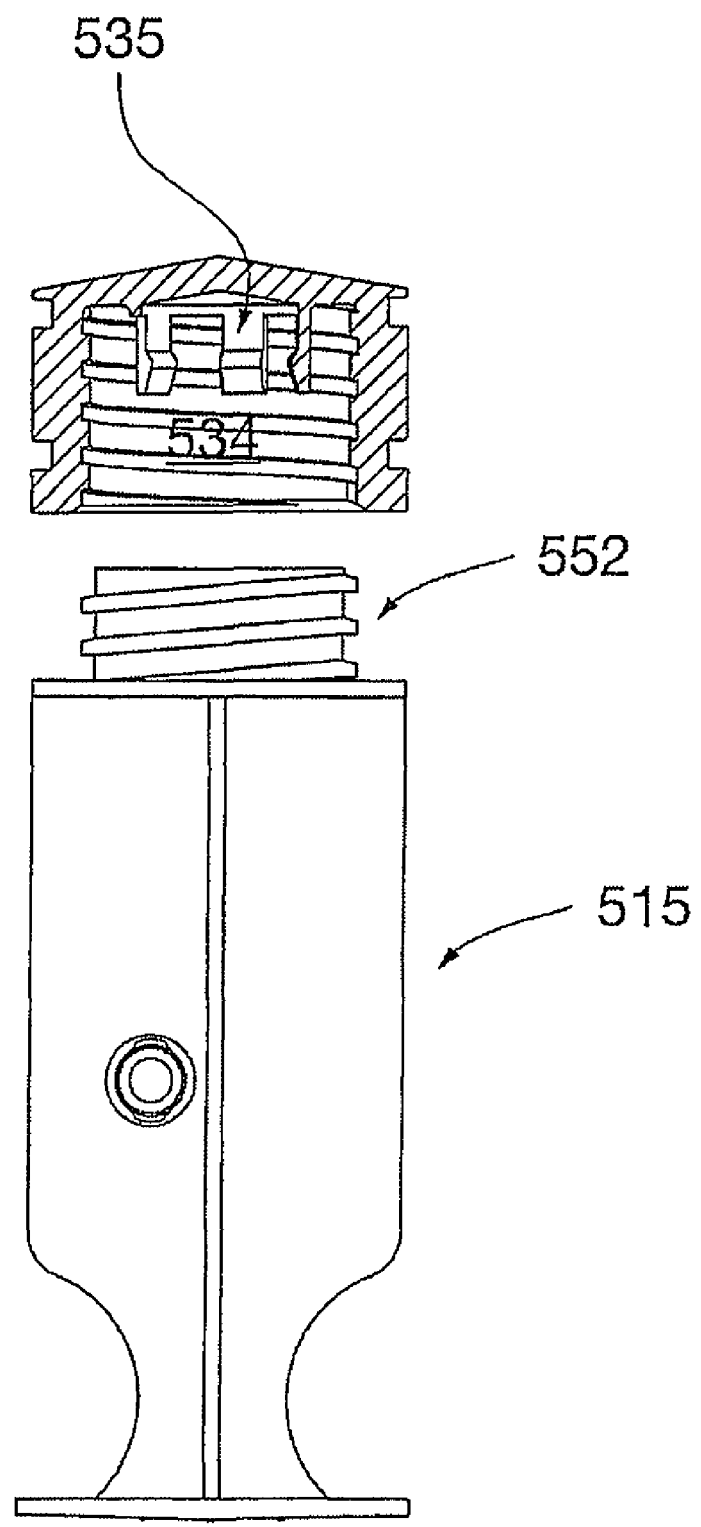
FIG. 4g is an exploded view of the plunger shown in FIG. 4f and of a syringe rod.

FIGS. 4f and 4g show a second variant embodiment of the plunger, here generally denoted 513.

Plunger 513 includes a seat 534 having a joint for head 37 of the pusher of a pump and a thread 540 for threaded head 552 of rod 515 of a syringe.

The joint defined inside seat 534 in plunger 513 is formed by four longitudinal extensions 535, substantially identical to the extensions described in connection with the first embodiment of the invention.

In this second variant embodiment, longitudinal extensions 535 preferably extend over only part of the length of seat 34, so as to leave an initial free portion for screwing rod 515.

Said rod 515 can comprise an axially bored threaded head 552, where said extensions 535 are received when rod 515 is wholly screwed into seat 534.

Thanks to this second variant embodiment of the invention, the coupling of the rod with the plunger may take place in conventional way, i.e. by screwing, while maintaining the coupling of the plunger onto the pusher through an axial translational movement.

The plunger according to the invention can be advantageously be used not only for a syringe where the liquid is to be previously drawn before the injection, but also for a phial already pre-filled with a liquid to be injected.

The invention claimed is:

1. A combination of a syringe plunger and a syringe rod configured to cooperate with said plunger, wherein said plunger comprises an engagement mechanism that retains a head of the rod at an end of an axial translational and rotary coupling of said plunger and said rod relative to each other;
   wherein said plunger comprises:
      a corresponding hollow cylindrical body with opposite cylindrical bases, and in which a dome closing one of the cylinder bases and an opening in the opposite base are defined;
      a circumferential groove provided around the cylindrical body of the plunger configured to accommodate a ring-shaped gasket,
      a seat provided inside the plunger and having defined therein a joint for the head of said rod;
   wherein said joint defined inside the seat of the plunger is formed by four longitudinal extensions, arranged along a circumference, mutually spaced apart by 90° and resiliently flexible in a radial direction towards an outside of seat; and
   wherein said rod comprises at a forward end configured to engage the plunger:
      a disc-shaped base from which a central cylindrical projection and a pair of arc-shaped projections, diametrically opposed and arranged externally of said central projection, extend axially upwards;
      a first pair of radial stops, radially extending from a forward base of said cylindrical projection;
      a second pair of axial stops extending from a wall of the cylindrical projection and joined to said disc-shaped base.

2. The rod as claimed in claim 1, wherein said radial stops are arranged along a diameter passing through the central axis of the cylindrical projection.

3. The rod as claimed in claim 1, wherein said axial stops are mutually offset so as to be arranged along two respective chords of the cylindrical projection.

4. The rod as claimed in claim 1, wherein the axial stops allow for a limited amount of rotation of the plunger and rod by preventing further rotation of the plunger and rod beyond a limit.

5. A syringe comprising a cylindrical hollow barrel and a plunger which is slidable within the syringe barrel in a first direction in order to draw liquid through a first opening provided at one end of the syringe barrel, and in a second direction in order to inject through the same opening the liquid previously drawn, wherein said plunger comprises an engagement mechanism for retaining the head of a rod at the end of an axial translational and rotary coupling movement of said plunger and said rod relative to each other; and
   wherein said plunger comprises:
      a corresponding hollow cylindrical body with opposite cylindrical bases, and in which a dome closing one of the cylinder bases and an opening in the opposite base are defined;
      a circumferential groove provided around the cylindrical body of the plunger configured to accommodate a ring-shaped gasket,
      a seat provided inside the plunger and having defined therein a joint for the head of said rod;
   wherein said joint defined inside the seat of the plunger is formed by four longitudinal extensions, arranged along a circumference, mutually spaced apart by 90° and resiliently flexible in a radial direction towards an outside of seat; and
   wherein said rod comprises at a forward end configured to engage the plunger:
      a disc-shaped base from which a central cylindrical projection and a pair of arc-shaped projections, diametrically opposed and arranged externally of said central projection, extend axially upwards;
      a first pair of radial stops, radially extending from a forward base of said cylindrical projection;
      a second pair of axial stops extending from a wall of the cylindrical projection and joined to said disc-shaped base.

6. The syringe as claimed in claim 5, said rod being removably connected to the plunger and projecting from the syringe barrel through a second opening formed at the end of the syringe barrel opposite to the first opening.

7. A phial pre-filled with a liquid, comprising a cylindrical hollow body and a plunger which is slidable within the phial body in order to inject the liquid through an opening provided at one end of the phial body, wherein said phial comprises a rod configured to cooperate with said plunger, wherein the plunger comprises an engagement mechanism that retains a head of the rod at an end of an axial translational and rotary coupling of said plunger and said rod relative to each other;
   wherein said plunger comprises:
      a corresponding hollow cylindrical body with opposite cylindrical bases, and in which a dome closing one of the cylinder bases and an opening in the opposite base are defined;
      a circumferential groove provided around the cylindrical body of the plunger configured to accommodate a ring-shaped gasket,
      a seat provided inside the plunger and having defined therein a joint for the head of said rod;

wherein said joint defined inside the seat of the plunger is formed by four longitudinal extensions, arranged along a circumference, mutually spaced apart by 90° and resiliently flexible in a radial direction towards an outside of seat; and wherein said rod comprises at a forward end configured to engage the plunger:
- a disc-shaped base from which a central cylindrical projection and a pair of arc-shaped projections, diametrically opposed and arranged externally of said central projection, extend axially upwards;
- a first pair of radial stops, radially extending from a forward base of said cylindrical projection;
- a second pair of axial stops extending from a wall of the cylindrical projection and joined to said disc-shaped base.

* * * * *